(12) United States Patent
Sheshbaradaran

(10) Patent No.: US 9,283,208 B2
(45) Date of Patent: Mar. 15, 2016

(54) MEDICAMENTS AND METHODS FOR TREATING CANCER

(75) Inventor: Hooshmand Sheshbaradaran, Hoboken, NJ (US)

(73) Assignee: NIIKI PHARMA INC., Hoboken, NJ (US)

( * ) Notice: Subject to any disclaimer, the term of this patent is extended or adjusted under 35 U.S.C. 154(b) by 0 days.

(21) Appl. No.: 14/117,456

(22) PCT Filed: May 17, 2012

(86) PCT No.: PCT/US2012/038230
§ 371 (c)(1),
(2), (4) Date: Nov. 17, 2014

(87) PCT Pub. No.: WO2012/158856
PCT Pub. Date: Nov. 22, 2012

(65) Prior Publication Data
US 2015/0080354 A1    Mar. 19, 2015

Related U.S. Application Data

(60) Provisional application No. 61/486,783, filed on May 17, 2011.

(51) Int. Cl.
| | | |
|---|---|---|
| *A01N 45/00* | (2006.01) |
| *A61K 31/56* | (2006.01) |
| *A01N 55/02* | (2006.01) |
| *A61K 31/555* | (2006.01) |
| *A61K 31/416* | (2006.01) |
| *A61K 9/00* | (2006.01) |
| *A61K 45/06* | (2006.01) |
| *A61K 9/19* | (2006.01) |
| *A61K 31/573* | (2006.01) |

(52) U.S. Cl.
CPC ............ *A61K 31/416* (2013.01); *A61K 9/0019* (2013.01); *A61K 9/19* (2013.01); *A61K 31/573* (2013.01); *A61K 45/06* (2013.01)

(58) Field of Classification Search
USPC .................................................. 514/171, 184
See application file for complete search history.

(56) References Cited

U.S. PATENT DOCUMENTS

| | | | |
|---|---|---|---|
| 7,338,946 B2 | 3/2008 | Keppler | |
| 2004/0235853 A1* | 11/2004 | Kyle et al. | 514/252.02 |
| 2005/0031648 A1* | 2/2005 | Brin et al. | 424/239.1 |
| 2010/0094019 A1 | 4/2010 | Keppler | |
| 2013/0253202 A1* | 9/2013 | Sheshbaradaran et al. | 548/108 |

FOREIGN PATENT DOCUMENTS

WO    WO-2010121245 A1    10/2010

OTHER PUBLICATIONS

Hudej et al., The Influence of Electroporation on Cytotoxicity of Anticancer Ruthenium (III) Complex KP1339 In Vitro and In Vivo, Anticancer Research, vol. 30, No. 6, No Month Listed 2010 (pp. 2055-2064).
International Search Report and Written Opinion issued by the Korean Intellectual Property Office as International Searching Authority for International Application No. PCT/US2012/038230 mailed Dec. 6, 2012 (12 pages).
Rademaker-Lakhai et al., "A Phase I and Pharmacological Study with Imidazolium trans-DMSO-imidazole-tetrachlororuthenate, a Novel Ruthenium Anticancer agent," Clinical Cancer Research, vol. 10, No. 11, Jun. 1, 2004 (pp. 3717-3727).

* cited by examiner

*Primary Examiner* — Marcos Sznaidman
(74) *Attorney, Agent, or Firm* — Kevin N. Sill

(57) ABSTRACT

Medicaments and methods for treating cancer are disclosed.

12 Claims, 2 Drawing Sheets

US 9,283,208 B2

MEDICAMENTS AND METHODS FOR TREATING CANCER

CROSS-REFERENCE TO U.S. APPLICATIONS

The present application is a national phase application under 35 U.S.C. §371 of International Application No. PCT/US2012/038230, filed May 17, 2012, which claims priority to U.S. Provisional Application No. 61/486,783 filed May 17, 2011, both of which are incorporated herein by reference.

FIELD OF THE INVENTION

This invention generally relates to a method of treating cancer, and particularly to a dosing regimen and dosing units comprising sodium trans-[tetrachlorobis(1H-indazole)ruthenate (III)].

BACKGROUND OF THE INVENTION

A number of ruthenate compounds are known in the art to be useful as anti-tumor compounds. See e.g., U.S. Pat. No. 4,843,069: PCT Publication No. WO 9736595, and US Application Publication No. 2005032801. In particular, the ruthenium complex salts indazolium trans-[tetrachlorobis(1H-indazole)ruthenate (III)] and sodium trans-[tetrachlorobis(1H-indazole)ruthenate (III)] have been shown to be highly potent in inducing apoptosis in certain types of cancer. See U.S. Pat. No. 7,338,946.

SUMMARY OF THE INVENTION

The present invention is at least in part based on the discovery of a minimum effective dose and a maximal tolerated dose of sodium trans-[tetrachlorobis(1H-indazole)ruthenate (III)] administered to a patient for treating cancer. The present invention is at least in part based on the discovery of a superior dosing schedule for intravenously administering sodium trans-[tetrachlorobis(1H-indazole)ruthenate (III)] to a patient for treating cancer.

Accordingly, in a first aspect, the present invention provides a pharmaceutical unit dosage form having greater than about 500 mg of sodium trans-[tetrachlorobis(1H-indazole)ruthenate (III)] and is substantially free of indazolium hydrochloride. Preferably, the pharmaceutical unit dosage form has from about 600 to about 1000 mg of sodium trans-[tetrachlorobis(1H-indazole)ruthenate (III)] and is substantially free of indazolium hydrochloride. Also preferably the pharmaceutical unit dosage form contains from about 650 to about 1000 mg of sodium trans-[tetrachlorobis(1H-indazole)ruthenate (III)]. The pharmaceutical unit dosage forms may be, e.g., lyophilized power in a vial. Relevant to this aspect, a medicament is also provided having from about 600 mg to about 1600 mg of sodium trans-[tetrachlorobis(1H-indazole)ruthenate (III)].

In another aspect, a method of treating cancer is provided comprising administering a pharmaceutical composition comprising sodium trans-[tetrachlorobis(1H-indazole)ruthenate (III)] intravenously to a patient in need of treatment of cancer at an amount of from greater than about 500 mg to about 1562.5 mg, preferably at an amount greater than about 600 mg. Also preferably, the pharmaceutical composition is substantially free of indazolium hydrochloride. In some embodiments, the sodium trans-[tetrachlorobis(1H-indazole)ruthenate (III)] is administered once a week, preferably once on each day 1, day 8 and day 15 of a 28-day or monthly cycle.

In another aspect, a method of treating cancer is provided, comprising administering a therapeutically effective amount of sodium trans-[tetrachlorobis(1H-indazole)ruthenate (III)] to a patient in need of treatment of cancer, intravenously on a dosing schedule of once a week, preferably on each day 1, day 8 and day 15 of a 28-day or monthly cycle. Preferably, sodium trans-[tetrachlorobis(1H-indazole)ruthenate (III)] is administered at an amount of at least about 320 mg/m$^2$ based on the body surface area (BSA) of the patient, preferably at an amount of from about 320 mg/m$^2$ to about 625 mg/m$^2$ based on the body surface area (BSA) of the patient.

The present invention also provides a method of treating cancer comprising administering to a patient in need of treatment the compound sodium trans-[tetrachlorobis(1H-indazole)ruthenate (III)] at an amount from about 320 mg/m$^2$ to about 625 mg/m$^2$ based on the body surface area (BSA) of the patient, preferably through intravenous infusion.

In yet another aspect, a method is provided for treating cancer comprising administering to a patient a medication for preventing infusional fever prior to the administration of sodium trans-[tetrachlorobis(1H-indazole)ruthenate (III)] intravenously to the patient. The fever-preventing drug may be a steroid such as prednisone or dexamethasone.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

Figure 1:
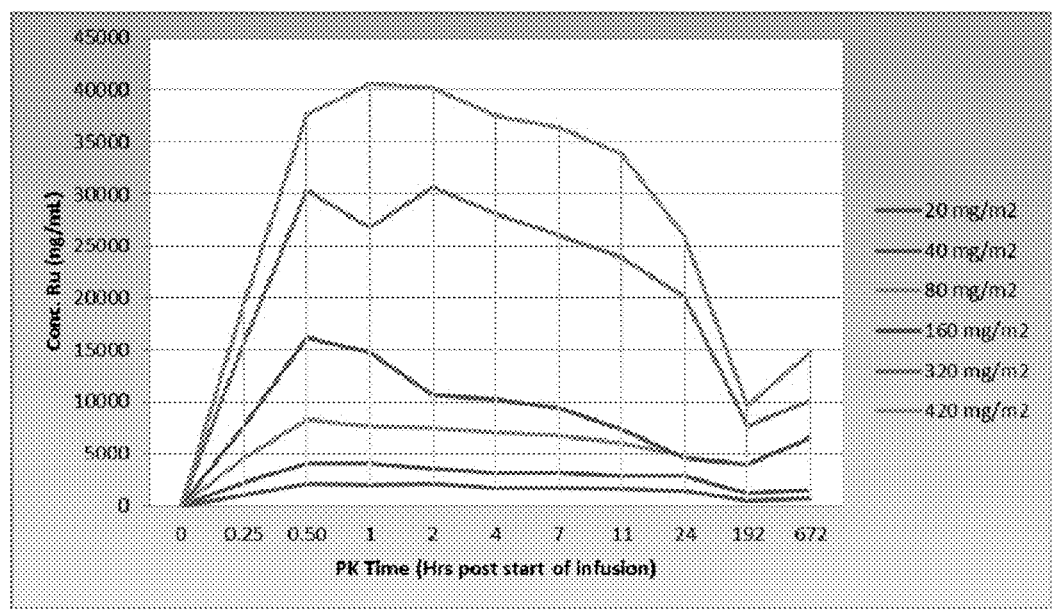
FIG. 1 is the PK curves arranged from the bottom to the top correspond to drug doses of 20 mg/m$^2$, 40 mg/m$^2$, 80 mg/m$^2$, 160 mg/m$^2$, 320 mg/m$^2$ and 420 mg/m$^2$, respectively.

The present invention provides a method of treating cancer, comprising administering a therapeutically effective amount of sodium trans-[tetrachlorobis(1H-indazole)ruthenate (III)] to a patient in need of treatment of cancer, intravenously on a dosing schedule of once a week. Preferably, the sodium trans-[tetrachlorobis(1H-indazole)ruthenate (III)] is in a pharmaceutical composition substantially free of indazolium hydrochloride. As used herein and in the description below, the term "substantially free of indazolium hydrochloride" means that in the pharmaceutical composition the molar ratio of sodium trans-[tetrachlorobis(1H-indazole)ruthenate (III)] to indazolium hydrochloride is at least 4 to 1. In preferred embodiments, the molar ratio of sodium trans-[tetrachlorobis(1H-indazole)ruthenate (III)] to indazolium hydrochloride is at least 10:1 or greater, and more preferably 20:1 or greater.

In some embodiments, sodium trans-[tetrachlorobis(1H-indazole)ruthenate (III)] is administered each time at an amount of at least about 400 or 500 mg, or at least about 320 mg/m$^2$ based on the body surface area (BSA) of the patient. In preferred embodiments, the patient is administered once on each of day 1, day 8 and day 15 of a 28-day cycle, preferably each at an amount of at least about 320 mg/m$^2$ based on the body surface area (BSA) of the patient, or at an absolute amount of at least about 400 or 500 mg. The BSA can be calculated using the Modified Dubois, i.e., BSA (m$^2$)= 0.007184×Height(cm)$^{0.725}$×Weight(kg)$^{0.425}$.

In preferred embodiments, the amount of sodium trans-[tetrachlorobis(1H-indazole)ruthenate (III)] administered to a patient at each administration, e.g., in the one time on day 1, is at least about 320 mg/m$^2$, preferably between about 320 mg/m$^2$ and about 625 mg/m$^2$.

The dosage range of from about 320 mg/m$^2$ and about 625 mg/m$^2$ was discovered during a human dose escalating clinical trial, from which 320 mg/m$^2$ was determined to be the minimum effective dosage for general use of treating cancer while 625 mg/m$^2$ was the maximal tolerated dose.

Thus, in another aspect, the present invention provides a method of treating cancer, comprising administering intravenously to a patient in need of treatment of cancer sodium trans-[tetrachlorobis(1H-indazole)ruthenate (III)] at an amount of at least about 320 mg/m$^2$, preferably between about 320 m g/m$^2$ and about 625 mg/m$^2$ based on the patient's BSA. The BSA of normal adults typically ranges from 1.5 to about 2.5 m$^2$. Thus, in some embodiments, a method of treating cancer comprises administering intravenously to a patient in need of treatment of cancer sodium trans-[tetrachlorobis (1H-indazole)ruthenate (III)] at an amount of about 400 mg to about 1600 mg, or about 400 mg to about 1500 mg, or about 400 mg to about 1400 mg, or about 400 mg to about 1200 mg, preferably 480 mg to about 1600 mg, 500 mg to about 1562.5 mg, preferably an amount that is greater than about 600 mg but preferably less than about 1600 mg. Preferably, sodium trans-[tetrachlorobis(1H-indazole)ruthenate (III)] is administered in a pharmaceutical composition that is substantially free of indazole hydrochloride. Preferably the pharmaceutical composition is administered once a week, and preferably once on each of day 1, day 8 and day 15 of a 28-day cycle. In some embodiments, sodium trans-[tetrachlorobis(1H-indazole)ruthenate (III)] is intravenously administered in an amount of greater than 600 mg, e.g., from greater than 600 mg to about 1200 mg. For example, in preferred embodiments, an amount of from greater than 600 mg to about 1200 or 1400 mg is administered intravenously once a week, or according to the following schedule: from greater than 600 mg to about 1200 or 1400 mg on day 1, from greater than 600 mg to about 1200 or 1400 mg on day 8, and from greater than 600 mg to about 1200 or 1400 mg on day 15 of a 28-day or monthly cycle. That is, after one 28-day or a month period, in which a patient is administered from greater than 600 mg to about 1200 or 1400 mg on days 1, 8 and 15 of that 28-day period, the same amount is administered to the patient on days 1, 8, and 15 of the next 28-day period, and repeating the administration cycle if necessary. In preferred embodiments, the sodium trans-[tetrachlorobis(1H-indazole)ruthenate (III)] is in a pharmaceutical composition substantially free of indazolium hydrochloride.

Figure 2:
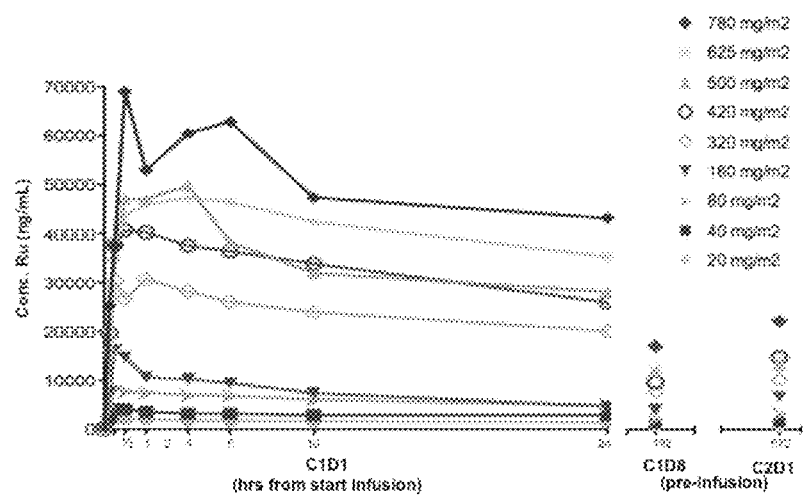
FIG. 2: Total ruthenium levels measured by ICP-MS. A) Plasma ruthenium levels for Cycle 1 Day 1 (C1D1), Cycle 1 Day 8 (C1D8) and Cycle 2 Day 1 (C2D1); B) drug dose proportionality of Cmax; C) drug dose proportionality AUC$_{0-24}$.
Figure 2:
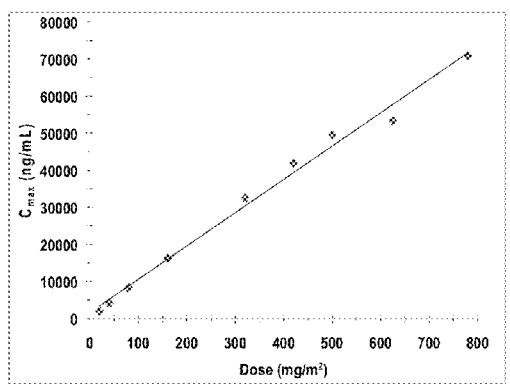
Figure 2:
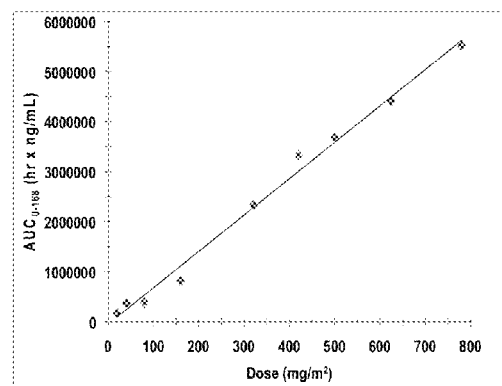

In another aspect, the present invention provides a method of treating cancer, comprising administering intravenously to a patient in need of treatment of cancer sodium trans-[tetrachlorobis(1H-indazole)ruthenate (III)] at an amount sufficient to arrive at a plasma $C_{max}$ of at least about 30 µg/ml and/or a plasma $AUC_{0-192}$ (AUC within the period of 192 hours after administration) of at least 2500 µg/ml·hr as measured by ruthenium (III). Preferably, the amount of sodium trans-[tetrachlorobis(1H-indazole)ruthenate (III)] is administered such that the plasma $C_{max}$ is less than about 50 µg/ml and/or a plasma $AUC_{0-192}$ (AUC within the period of 192 hours after administration) of less than about 4500 µg/ml·hr as measured by ruthenium (III). FIGS. 1-2 show the pharmacokinetics behavior of sodium trans-[tetrachlorobis(1H-indazole)ruthenate (III)] in patients. In preferred embodiments, the sodium trans-[tetrachlorobis(1H-indazole)ruthenate (III)] is in a pharmaceutical composition substantially free of indazolium hydrochloride.

Sodium trans-[tetrachlorobis(1H-indazole)ruthenate(III)] can be made in any methods known in the art. For example, PCT Publication No. WO/2008/154553 discloses an efficient method of making sodium trans-[tetrachlorobis(1H-indazole)ruthenate(III)].

In accordance with the present invention, it is provided a use of sodium trans-[tetrachlorobis(1H-indazole)ruthenate (III)] at an amount of from about 400 mg to about 1200 mg, about 1500 mg or about 2000 mg, preferably from more than 500 mg to about 1000 mg or 1200 mg, more preferably from about 600 mg or 650 mg to about 1000 mg or 1200 mg for the manufacture of an intravenously injectable medicament useful for treating cancer. Injectable forms are generally known in the art, e.g., in buffered solution or suspension.

In another aspect, the present invention provides a pharmaceutical unit dosage form having greater than about 500 mg of sodium trans-[tetrachlorobis(1H-indazole)ruthenate (III)] and is substantially free of indazolium hydrochloride. Preferably, the pharmaceutical unit dosage form has from about 600 mg or 650 mg to about 1600 mg, preferably from about 600 to about 1000 mg of sodium trans-[tetrachlorobis (1H-indazole)ruthenate (III)] and is substantially free of indazolium hydrochloride. The pharmaceutical unit dosage forms may be, e.g., lyophilized power in a vial. A medicament is also provided having from about 600 mg to about 1600 mg of sodium trans-[tetrachlorobis(1H-indazole)ruthenate (III)].

It has been discovered that at therapeutically effective doses, intravenous infusion of sodium trans-[tetrachlorobis (1H-indazole)ruthenate (III)] is associated with a higher incidence of fever or chill, which can be prevented by premedication with steroids. Thus, in another aspect, a method is provided for treating cancer comprising administering to a patient a medication effective for preventing or reducing infusional fever, and thereafter administering a therapeutically effective amount of sodium trans-[tetrachlorobis(1H-indazole)ruthenate (III)]. The interval between the two different administrations may be from 0 to about 2 hours, preferably between 30 minutes and 1 hour. To put it differently, the invention provides the use of sodium trans-[tetrachlorobis (1H-indazole)ruthenate (III)] for the manufacture of a medicament for treating a cancer patient who has been treated with a medication effective for preventing or reducing infusional fever, e.g., within the previous 30 minutes to about 2 hours. Medications for preventing or ameliorating fever are known in the art. Steroids are most often used, e.g., prednisone and dexamethasone, which are well known drugs, and a skilled artisans should know how to administer such drugs for purposes of preventing or reducing fever. For example, dexamethasone may be administered IV at an amount of 4-10 mg. Additional premedications such as 5HT3 antagonists (serotonin antagonists) like ondansetron and granisetron may also be administered prior to the administration of sodium trans-[tetrachlorobis(1H-indazole)ruthenate (III)].

In yet another aspect, the invention provides a method of treating head and neck cancer, particularly head and neck carcinoma, comprising administering to a patient in need of treatment an effective amount of sodium trans-[tetrachlorobis (1H-indazole)ruthenate (III)]. In one embodiment, the head and neck cancer patient has previously been treated with a platinum agent, e.g., carboplatin, and/or a taxane (e.g., paclitaxel, docetaxol). The patient may be resistant to, or refractory to, such other agents. The amount of sodium trans-[tetrachlorobis(1H-indazole)ruthenate (III)] to be used may be according to the amount described herein.

EXAMPLE

Two Phase I dose-escalation clinical studies involving sodium trans-[tetrachlorobis(1H-indazole)ruthenate (III)] ("test drug") have been conducted. The primary objective of both studies is to determine the safety, tolerability and maximal tolerated dose (MTD) of the test drug. Secondary objectives are to estimate the PK parameters, to identify any preliminary evidence of anti-tumor activity of the test drug in patients with advanced cancers, and to explore pharmacodynamic (PD) endpoints which may be of use in the further development of the test drug.

In the first trial which has been conducted in two centers in the US, the "test drug" was given intravenously once a week, i.e., on days 1, 8, and 15 of each 28-day cycle to patients with advanced solid tumors refractory to treatment. The patients had advanced solid tumors that had been heavily treated previously, had failed an average of 7 previous lines of chemotherapy, and had progressing disease at the time of entry into the trial. Standard 3+3 design with expanded cohort up to 25 patients at the maximal tolerated dose (MTD).

Major Inclusion/Exclusion Criteria:
Patients≥18 years with histologically or cytologically confirmed advanced solid tumors refractory to standard therapies
ECOG PS 0 or 1
Adequate hematologic, hepatic and renal function
No symptomatic CNS metastases, no primary brain tumors
No evidence of ischemia, recent MI, or significant abnormality on ECG
No Peripheral neuropathy ≥Grade 2
Minimum life expectancy ≥12 weeks
Definition of Dose Limiting Toxicity (DLT):
Toxicity severity graded according to the CTCAE (ver. 3.0); occurring during Cycle 1 and related to test drug:
Grade 4 neutropenia for ≥7 days
Febrile neutropenia
Grade 4 thrombocytopenia or Grade
≥Grade 2 neurotoxicity
≥Grade 2 cardiotoxicity
Grade 2 hypersensitivity reaction or infusion reaction
Any other non-hematologic Grade 3 or 4 toxicity other than nausea/vomiting or alopecia
Inability to complete the first cycle due to any toxicity thought to be related to test drug.

The demographics of the patients enrolled are summarized in Table 1 below:

TABLE 1

| Patients enrolled to date | | N = 46 | |
|---|---|---|---|
| Gender | Male/Female | 25/21 | |
| Age, years | Median (Range) | 61 years (28-78 years) | |
| Race | Caucasian/Black/Other | 42/3/1 | |
| Number of prior systemic therapies | Median (Range) Unknown | 4 (0-8)* 14 | |
| Tumor type | CRC | 11 | Thymic | 1 |
| | NSCLC | 9 | Sarcoma | 1 |
| | Neuroendocrine (NET) | 5 | SCLC | 1 |
| | H&N | 4 | Adrenal | 1 |
| | Breast | 3 | Cholangiocarcinoma | 1 |
| | Pancreatic | 2 | Cervical | 1 |
| | Ovarian | 2 | Unknown primasy | 1 |
| | GE Junction | 2 | | |

Table 2 summarizes the patients enrolled.

TABLE 2

Enrollment

| Dose level (mg/m²) | Patients dosed | Patients w/ DLT | Patients replaced in due to PD in Cycle 1 |
|---|---|---|---|
| 20 | 1 | | |
| 40 | 1 | | |
| 80 | 1 | | |
| 160 | 1 | | |
| 320 | 7 | 1 | 1 |
| 420 | 5 | | 2 |
| 500 | 3 | | |
| 625 | 6 | 1 | |
| 780 | 9 | 3 | 1 |
| Expanded Cohort (625) | 12 | NA | |

DLT dose was set at 780 mg/m² and MTD was set at 625 mg/m² due to the dose limiting toxicity seen in 3 patients at the 780 mg/m² dose level:

TABLE 3

DLT Seen at 780 mg/m²

| 780 mg/m² | A 78 year old female had Grade 2 nausea, Grade 1 vomiting, Grade 1 fatigue following Cycle 1 Day 1 dosing associated with a Grade 2 creatinine elevation which returned to baseline within 1 week. |
| | 69 year old female had Grade 3 vomiting and Grade 3 dehydration following Cycle 1 Day 1 dosing associated with Grade 2 creatinine elevation which returned to baseline within 3 weeks. |
| | A 53 year old male had an infusion reaction consisting of fever and chills. He had not been premedicated with steroids |

36 pts completed ≥one cycle of therapy and are evaluable to assess antitumor efficacy. In this heavily pretreated population, efficacy was assessed by partial response or stable disease for ≥12 weeks. All patients had PD at study entry. Table 4 summarizes the patients who had response (either partial response (PR) or stable disease (SD)).

TABLE 4

| Dose level (mg/m²) | Total drug (mg) | Primary Tumor Type | # of Prior systemic therapies | Response | Duration of therapy |
|---|---|---|---|---|---|
| 320 | 531 | NSCLC | 7 | SD | 16 weeks |
| 320 | 630 | NET | 3 | PR | 100+ weeks |
| 320 | 618 | NSCLC | 4 | SD | 16 weeks |
| 420 | 832 | NET | 0* | SD | 24 weeks |
| 500 | 890 | Unknown primary | 2 | SD | 22 weeks |
| 625 | 1175 | GE Junction | 3 | SD | 12+ weeks |
| 625 | 1190 | CRC | 3 | SD | 12 weeks |
| 780 | 1450 | Sarcoma | 3 | SD | 16 weeks |
| 780 | 1544 | NET | 1 | SD | 27+ weeks |

*Failed 4 prior chemo- and Yttrium-embolization procedures

The second trial was conducted in two centers in the United Kingdom (UK) with the test drug being administered on days 1 through 4 of each 21-day cycle to patients with advanced solid tumors refractory to treatment. The patients had been heavily pre-treated and had failed an average of 3 previous lines of chemotherapy. Dose escalation progressed from 20 to 500 mg/m².

Table 5 sums up the detailed results in the UK trial.

TABLE 5

| Patient* # | Dose mg/m² | Tumor | # weeks of treatment | Anti-tumor effect (best response) |
|---|---|---|---|---|
| 1 | 20 | Esophageal | 2 | PD |
| 2 | 40 | Head & Neck | 4 | Stable disease |
| 3 | 80 | Mesothelioma | 2 | PD |
| 4 | 160 | Cecum | 2 | PD |
| 5 | 320 | Anal | 1 | PD |
| 6 | 500 | Rectal | 4 | Stable disease |
| 7 | 500 | Esophageal | 2 | PD |

As can be seen in Tables 4 and 5, stable disease was achieved in a large number of heavily pretreated patients. In particular, tumor regression was seen in the US trial in a carcinoid tumor patient who had been heavily treated with various chemotherapeutics, and had failed all such prior treatment. Sodium trans-[tetrachlorobis(1H-indazole)ruthenate (III)] was administered at 320 mg/m² on day 1, day 8 & day 15 of each 28-day cycle to the patient with stage 1V carcinoid tumor of small intestine. CT scan of target lesions was performed at baseline (BL) and end of every second cycle. The patient has been treated for over 100 weeks as of today, and the scans confirmed tumor regression and partial response. The patient still remains in the trial on the test drug as no tumor progression has occurred as of today. No major adverse event related to the test drug has been seen.

Head & Neck Patient: Among the treated patients was a 72 year old white male with head & neck carcinoma, adenocystic histology, completely resected in April 2003. This was Initial therapy consisted of radiotherapy (total dose 64 Gy) to the soft palate between May 2003 and July 2003 after which he achieved a partial response. Between October 2008 and February 2009, he received 6 cycles of carboplatin and paclitaxel with best response stable disease. Upon disease progression, therapy with carboplatin and paclitaxel was resumed with the addition of reolysin June 2009 through August 2009. His best response was progressive disease. The test drug was administered at 40 mg/m² on days 1 through 4 of each 21-day cycle. The treatment was initiated January 2010. The patient received 4 cycles of the test drug and stable disease was achieved in the patient.

Premedication: At the dose of 320 mg/m² and above, adverse reactions such as fever and chill were seen in the UK trial. Thereafter, in the US trial, in some patients, premedication of decadron (dexamethasone) was administered, with or without 5HT3 antagonists (serotonin antagonists) like ondansetron and granisetron. The decadron was given to prevent fever, at 4-10 mg IV. It was found that decadron was effective in preventing infusional fever. None of the patients premedicated with decadron had any incidence of infusion-related fever. In contrast, patients without premedication had a high likelihood of infusional fever. See Table 6 below.

TABLE 6

| | steroid premedication | | no steroid premedication | |
|---|---|---|---|---|
| dosage | # of patients | # with fever | # of patients | # with fever |
| 320 mg/m² | 4 | 0 | 3 | 0 |
| 420 mg/m² | 2 | 0 | 3 | 2* |
| 500 mg/m² | 2 | 0 | 1 | 1 |
| 625 mg/m² | 10 | 0 | 8 | 1 |
| 780 mg/m² | 6 | 0 | 3 | 1 |

*one with no premeds, the one had fever but then none after premed of additional doses Pharmacokinetics: PK samples were obtained 0, 0.25, 0.5, 1, 2, 4, 6-8, 10-12, and 24 hours after the start of the infusion on Cycle 1 Day 1 as well as pre-infusion on Cycle 1 Day 8 and Cycle 2 Day 1. Plasma and urine were analyzed for total ruthenium [Ru] (free and bound). Selected PK data is provided in Tables 7 and 8. FIG. 1 shows the plasma Ru levels over an extended period of time for doses of up to 420 mg/m². Peak plasma Ru levels were achieved by hour 2 (FIG. 2A). There is accumulation of Ru following dosing noted by Cycle 1 Day 8 and Cycle 2 Day 1 levels. The estimated T½ is 91.4-112 hours.

TABLE 7

Selected PK Concentrations and Trough Values for the test drug

| Dose Level | C1D1 Hour 24 ng/mL Ru | C1D8 Hour 0 ng/mL Ru | C2D1 Hour 0 ng/mL Ru |
|---|---|---|---|
| 20 mg/m² | 1366 | 528 | 670 |
| 40 mg/m² | 2884 | 1197 | 1472 |
| 80 mg/m² | 4831 | ND | ND |
| 160 mg/m² | 4639 | 4000 | 6588 |
| 320 mg/m² | 20033 | 7667 | 10126 |
| 420 mg/m² | 25921 | 9595 | 14698 |
| 500 mg/m² | 28070 | 11880 | 13000 |
| 625 mg/m² | 35216 | 12303 | 14363 |
| 780 mg/m² | 43105 | 17001 | 22125 |

There is good dose proportionality of $C_{max}$ and $AUC_{0-168}$ (Table 8 and FIG. 2 B, C). In the 24 hours following Cycle 1 Day 1 dosing, there is low urinary excretion of the test drug derived ruthenium.

TABLE 8

Ru $C_{max}$, $T_{max}$ and $AUC_{0-168}$ values for the test drug

| Dose | $C_{max}$ (ng/mL) (SD) | $T_{max}$ (hr) (SD) | $AUC_{0-68}$ (hr*ng/mL) (SD) | % of Dose Excreted in 24 hr[1] (SD) |
|---|---|---|---|---|
| 20 mg/m2 | 2111 (na) | 2.0 (na) | 175400 (na) | BLQ |
| 40 mg/m2 | 4055 (na) | 0.5 (na) | 366500 (na) | BLQ |
| 80 mg/m2 | 8292 (na) | 0.5 (na) | 382300 (na) | BLQ |
| 160 mg/m2 | 16180 (na) | 0.5 (na) | 808200 (na) | BLQ |
| 320 mg/m2 | 32350 (6516) | 1.57 (1.24) | 2328000 (544800) | 0.132 (0.051) |
| 420 mg/m2 | 42020 (12150) | 2.5 (2.6) | 3331000 (743300) | 0.117 (0.042) |
| 500 mg/m2 | 49760 | | 3674000 | |
| 625 mg/m2 | 53220 | | 4403000 | |
| 780 mg/m2 | 71010 | | 5516000 | |

[1]% of dose excreted in first 24 hr after Dose 1, Cycle 1
na: n = 1, SD value not applicable
BLQ: Below the Limit of Quantitation; amount excreted too low to be detected

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be apparent that certain changes and modifications may be practiced within the scope of the appended claims.

What is claimed is:

1. A method of treating neuroendocrine cancer, comprising administering to a patient in need thereof, a pharmaceutical unit dosage form comprising greater than about 500 mg of sodium trans-[tetrachlorobis(1H-indazole)ruthenate (III)] and is substantially free of indazolium hydrochloride wherein the dosage form is administered to the patient intravenously on a dosing schedule of once a week.

2. The method of claim 1, wherein the patient is administered the dosage form once on each day 1, day 8 and day 15 of a 28-day or monthly cycle.

3. The method of claim 2, wherein the dosage form is administered at an amount of at least about 320 mg/m$^2$ based on the body surface area of said patient.

4. The method of claim 3, wherein the dosage form is administered at an amount of from about 320 mg/m$^2$ to about 625 mg/m$^2$ based on the body surface area of said patient.

5. The method of claim 1, further comprising the step of administering to the patient a medication for preventing infusional fever prior to the administration of the dosage form.

6. The method of claim 5, wherein the medication for preventing infusional fever is a steroid.

7. The method of claim 6, wherein said steroid is prednisone or dexamethasone.

8. The method of claim 1, wherein the patient plasma $C_{max}$ is less than about 50 μg/mL.

9. The method of claim 1, wherein said cancer is associated with a solid tumor refractory to treatment.

10. The method of claim 1, wherein the treating results in stable disease in the patient.

11. The method of claim 1, wherein the pharmaceutical unit dosage form comprises from about 600 to about 1000 mg of sodium trans-[tetrachlorobis(1H-indazole)ruthenate (III)] and is substantially free of indazolium hydrochloride.

12. The method of claim 1, wherein said unit dosage form is a kophilized powder in a vial.

* * * * *